(12) United States Patent
Manigel et al.

(10) Patent No.: US 8,225,788 B2
(45) Date of Patent: Jul. 24, 2012

(54) MODULAR RESPIRATION SYSTEM FOR THE MECHANICAL RESPIRATION OF A PATIENT

(75) Inventors: Jürgen Manigel, Scharbeutz-Klingberg (DE); Bernhard Ludwig, Lübeck (DE); Götz Kullik, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 961 days.

(21) Appl. No.: 12/036,394

(22) Filed: Feb. 25, 2008

(65) Prior Publication Data
US 2008/0264417 A1    Oct. 30, 2008

(30) Foreign Application Priority Data
Apr. 25, 2007    (DE) .................... 10 2007 019 487

(51) Int. Cl.
*A61M 16/00*  (2006.01)
*A61M 15/00*  (2006.01)
*A62B 7/00*    (2006.01)
*A62B 9/04*    (2006.01)
(52) U.S. Cl. ......... 128/204.21; 128/200.24; 128/204.18; 128/205.11; 128/205.27; 128/205.28; 128/202.27
(58) Field of Classification Search ............ 128/200.24, 128/204.18, 204.21, 204.22, 204.23, 204.25, 128/205.11
See application file for complete search history.

(56) References Cited

U.S. PATENT DOCUMENTS

| | | | | | |
|---|---|---|---|---|---|
| 4,883,051 A | * | 11/1989 | Westenskow et al. | ... | 128/204.21 |
| 5,253,640 A | * | 10/1993 | Falb et al. | ................ | 128/200.24 |
| 5,673,688 A | * | 10/1997 | Tham et al. | .............. | 128/204.22 |
| 5,694,924 A | * | 12/1997 | Cewers | ..................... | 128/204.21 |
| 5,806,513 A | * | 9/1998 | Tham et al. | .............. | 128/204.22 |
| 5,857,458 A | * | 1/1999 | Tham et al. | .............. | 128/203.28 |
| 6,024,087 A | * | 2/2000 | Kersey et al. | ............ | 128/203.12 |
| 6,095,138 A | * | 8/2000 | Hognelid et al. | ......... | 128/204.18 |
| 6,119,686 A | * | 9/2000 | Somerson et al. | ........ | 128/202.22 |
| 6,158,430 A | * | 12/2000 | Pfeiffer et al. | ............ | 128/202.27 |
| 6,213,120 B1 | * | 4/2001 | Block et al. | ............. | 128/204.23 |
| 6,553,990 B2 | * | 4/2003 | Hoffmann | ................ | 128/203.12 |
| 6,668,824 B1 | * | 12/2003 | Isaza et al. | ............... | 128/202.22 |

* cited by examiner

*Primary Examiner* — Annette Dixon
(74) *Attorney, Agent, or Firm* — McGlew and Tuttle, P.C.

(57) ABSTRACT

A modular respiration system is provided for the mechanical respiration of a patient. The respirator system has a modular respiration module (1) for connection to the patient (20), wherein the respiration module (1) contains a respiration system (30) with a respiration drive (3), an electric energy unit (5) and a memory with a control unit (ES II). One or more stationary parts (2) are provided for detachably accommodating the complementary modular respiration module (1). At least one detachable connection interface (8) is provided for data, electric energy and breathing gas exchange between the respiration module (1) and the stationary part or parts (2) accommodating the respiration module (1).

16 Claims, 3 Drawing Sheets

MODULAR RESPIRATION SYSTEM FOR THE MECHANICAL RESPIRATION OF A PATIENT

CROSS REFERENCE TO RELATED APPLICATIONS

This application claims the benefit of priority under 35 U.S.C. §119 of German Patent Application DE 10 2007 019 487.2 filed Apr. 25, 2007, the entire contents of which are incorporated herein by reference.

FIELD OF THE INVENTION

The present invention pertains to a modular respiration system for the mechanical respiration of a patient.

BACKGROUND OF THE INVENTION

There are currently various special devices for respirating patients, which are optimized for the particular task. The most important prior-art embodiments are portable respirators, intensive respirators and anesthesia devices with rebreathing systems.

Depending on the particular situation, it is therefore necessary during mechanical respiration for the patient to be separated or disconnected from one device and connected to another device. This operation requires a separation either between the tube or mask, and the breathing tube system on the patient side of that system, or between the device and the breathing tube system on the device side of that system. Mechanical respiration is interrupted in both cases and there always is a loss of pressure in the lungs. The operation is critical, and the loss of pressure leads to collapse of the lungs and hence to a worsening of the patient's condition in the case of many patients who require mechanical respiration.

In addition, respiration is not being monitored by means of pressure sensors during the changeover time. If the changeover operation takes longer, manual respiration is, moreover, necessary by means of a manual breathing bag. For example, the following changeover scenarios with transporting of a patient and corresponding changeovers of the respirators are possible or necessary during a hospitalization:

Emergency department/intensive care unit;
Emergency department/surgical area/intensive care unit;
Changeover between intensive care unit and various diagnostic environments, such as computed tomography (CT) or nuclear spin tomography (NMR);
Changeover between intensive care unit and surgical area; and
Changeover in the surgical area from the preparation for the surgery via the surgery to the recovery area.

There is a need for frequent transportation with the more or less painful and unpleasant changeovers from one device to another and reconnection operations associated therewith especially in case of severely ill patients because of the differential diagnostic examinations to be performed in stationary special installations such as CT, NMR or in the cardiac catheterization laboratory.

SUMMARY OF THE INVENTION

The object of the present invention is to provide a respiration system, which makes it possible to continue the mechanical respiration of the patient without interruption even in case of change in place and during specific treatments taking place during the respiration in various medical environments.

According to the invention, a modular respiration system is provided for the mechanical respiration of a patient. The modular respiration system comprises a mobile respiration module for the connection to the patient. The mobile respiration module includes a respiration system with a respiration drive, an electrical energy supply unit and a memory with a control unit. A stationary part is provided with accommodation means for detachably accommodating the complementary mobile respiration module. The stationary part includes a detachable connection interface for exchange of data, electric energy and breathing gases between the mobile respiration module and the stationary part or part with means for detachably accommodating the respiration module.

The respiration system of the respiration module may further comprise an inspiration branch with the respiration drive, with a pressure relief valve and with breathing tubes to and from the patient when viewed in the direction of flow. The respiration system of the respiration module may also include an expiration branch with a positive end expiratory pressure (PEEP) valve and a non-return valve arranged in or connected to the inspiration branch. The connection interface may have a connection interface portion for the inspiration branch and for the expiration branch.

The connection interface may include ports that are closed when the respiration module has been mechanically accommodated in the stationary part.

The mobile respiration module may include an operating device and at least one of a sensor part and a display part.

The respiration system of the respiration module may further comprise an inspiration branch and an expiration branch wherein the mobile respiration module has a first pressure sensor and a first non-return valve operatively connected to the inspiration branch and a second pressure sensor and a second non-return valve operatively connected to the expiration branch. The stationary part may comprise a rebreathing system and may have a first flow sensor with a manual breathing bag and an airway pressure limit (APL) valve inserted between the first flow sensor and the manual breathing bag and with an excess gas discharge line as well as a $CO_2$ absorber connected to the manual breathing bag and with a second flow sensor in the expiration line in the direction of flow. The stationary part may also be an open respiration system and comprise a mixing chamber for ambient air and the fresh gas an inspiratory flow sensor a breathing gas moistener and/or an occlusive valve in the inspiration line in the direction of flow; and an outlet-side expiratory flow sensor with outlet to the ambient air or into an expiration gas discharge line in the expiration line.

The respiration drive may advantageously be a radial flow compressor that is actuated electrically.

An essential advantage of the respiration system according to the invention is that uninterrupted mechanical respiration can take place during the entire transportation and process chain for the patient within the hospital, especially also during anesthesia, and that easy handling of the one mobile respiration module by the user is possible.

The consequence of the uninterrupted mechanical respiration is that there is no accidental loss of pressure in the lungs, which would subsequently lead to a disadvantageous collapse of the lungs.

The mobile respiration module can be separated from the complementary stationary part by the user very easily especially by detaching corresponding mechanical connection elements.

The stationary parts of the entire modular respiration system are available in various variants, which are adapted to the particular needs for transportation within the hospital, stationary intensive respiration or anesthesia. Together with the mobile respiration module, full-fledged medical workstations are obtained for transportation, intensive respiration or anesthesia.

Each stationary part of the overall system has a control unit with a memory, a display part and operating device as well as supply means for electric energy and gas. It can be switched on and off and tested independently from the mobile respiration module.

The mobile respiration module has a respiration system with a respiration drive, optionally with a sensor part, with an electric energy unit and with a memory with a control device.

After connection to or accommodation in a stationary part, the mobile respiration module is recognized by the stationary part of the respiration system and connected to the display part and operating device immediately or after start-up of the stationary part. The data and energy supply of the mobile respiration module is ensured by the stationary part immediately after connection or accommodation.

After disconnection of the mobile respiration module, it continues to respirate the connected patient autarchically in exactly the same manner as before in connection with the stationary part.

The connection interfaces between the respiration module and the stationary part accommodating the respiration module connect breathing gas ports for inspiration and expiration as well as the electrical components to electric energy and data.

The interfaces are embodied mechanically such that the connection or accommodation and separation can be carried out in no time. An accidental separation is ruled out by a mechanical interlock.

Increased oxygen supply is allowed by a special embodiment of the gas ports.

It is especially advantageous in this connection to embody the electrical data and energy transmission by means of inductive components with coils and corresponding inductances with iron short-circuit and entirely without electrically conductive components.

Exemplary embodiments of the modular respiration system will be explained below by means of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENTS

Figure 1:
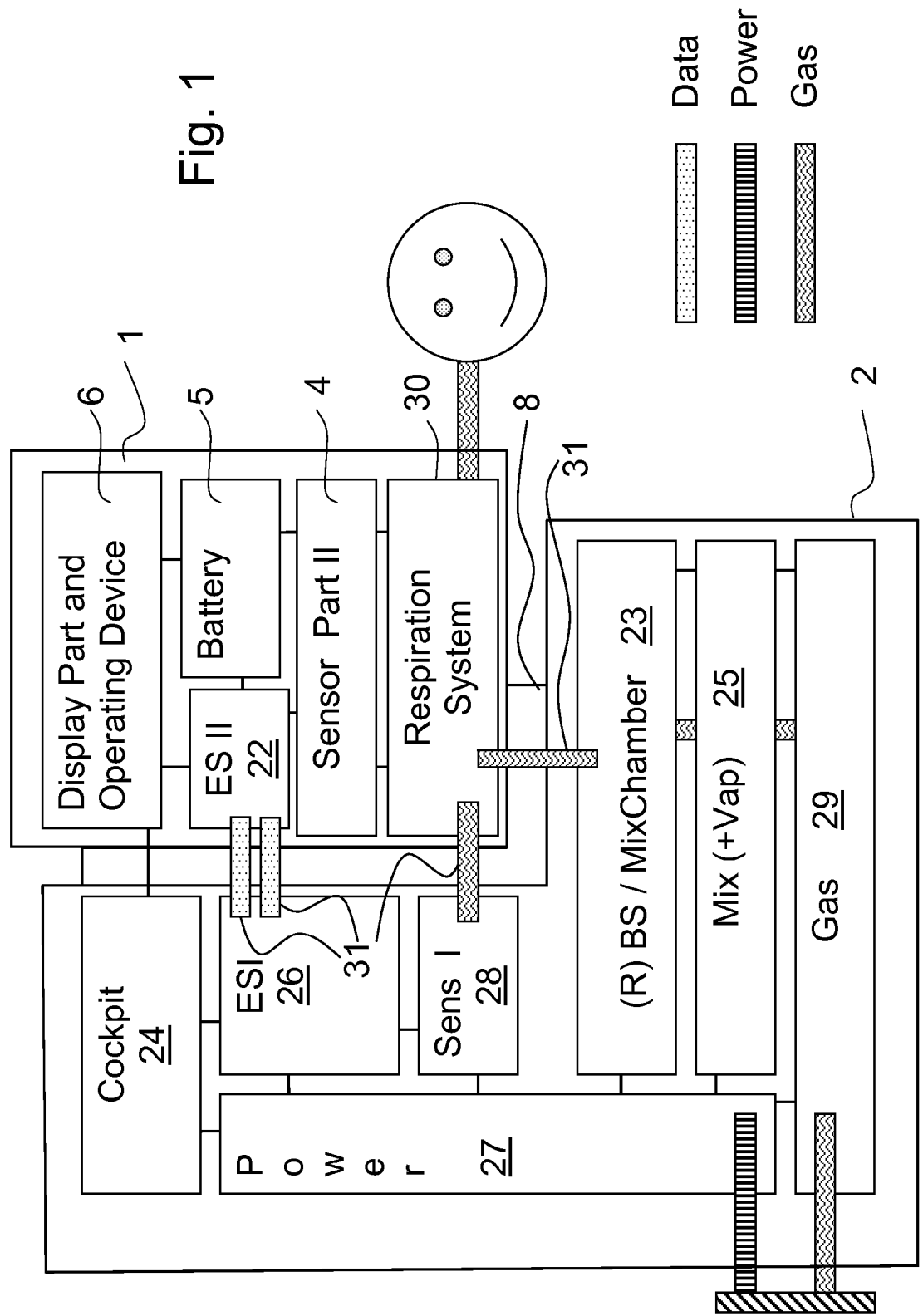
FIG. 1 is a block diagram of a respiration module according to the invention with integration in a stationary part.

Referring to the drawings in particular, a respiration module 1, which is arranged in the top right part in FIG. 1 and which has a edge, preferably contains a simple display part and operating device 6, a sensor part 4 for measuring and monitoring respiration parameters, especially the respiration pressure, and a respiration system 30 as well as an electric energy unit 5 and preferably a memory as well as a control unit 22 ("ES II"). The stationary part 2, which is shown on the left-hand side and at the bottom, has a "cockpit" 24 as a workstation display part and operating device, an "embedded system ESI" 26 as a memory and control unit for the tasks that are to be performed on the stationary part 2, for example, the setting of alarm limits, a sensor unit "Sens I" 28 for the sensors of the stationary part, for example, for expiration flow and gaseous anesthetic concentration, a respiration system part 23, which is embodied either for anesthesia with a rebreathing circuit ("(R)BS") or otherwise as a mixing chamber for oxygen ("MixChamber").

In addition to this, there are components 25 for mixing gases ("Mix") and for evaporating anesthetics ("+Vap") as well as supply units for electric energy ("Power") 27 and breathing gas ("Gas") 29, which are connected to the infrastructure of the hospital or optionally to corresponding portable storage devices.

The mobile respiration module 1 and the complementary stationary part 2 have connections or ports 31 between one another for breathing gas, electric energy and data in the form of an interface 8, which can be operated in a simple manner, and the patient 20 is connected to the respiration system 30.

The mobile respiration module 1, which is always the same, can be connected to stationary parts 2 that have specifically different designs or configurations. Thus, the respiration module 1 may be connected to a stationary part 2 in an emergency department (ED), in the operating room (Perioperative Care, POC), in the intensive care unit (Critical Care, CC), or, for example, at the Nuclear Spin Tomograph (Nuclear Magnetic Resonance, NMR). A corresponding "stationary part" 2 is provided for the transportation task for exclusive supply during transportation.

Figure 2:
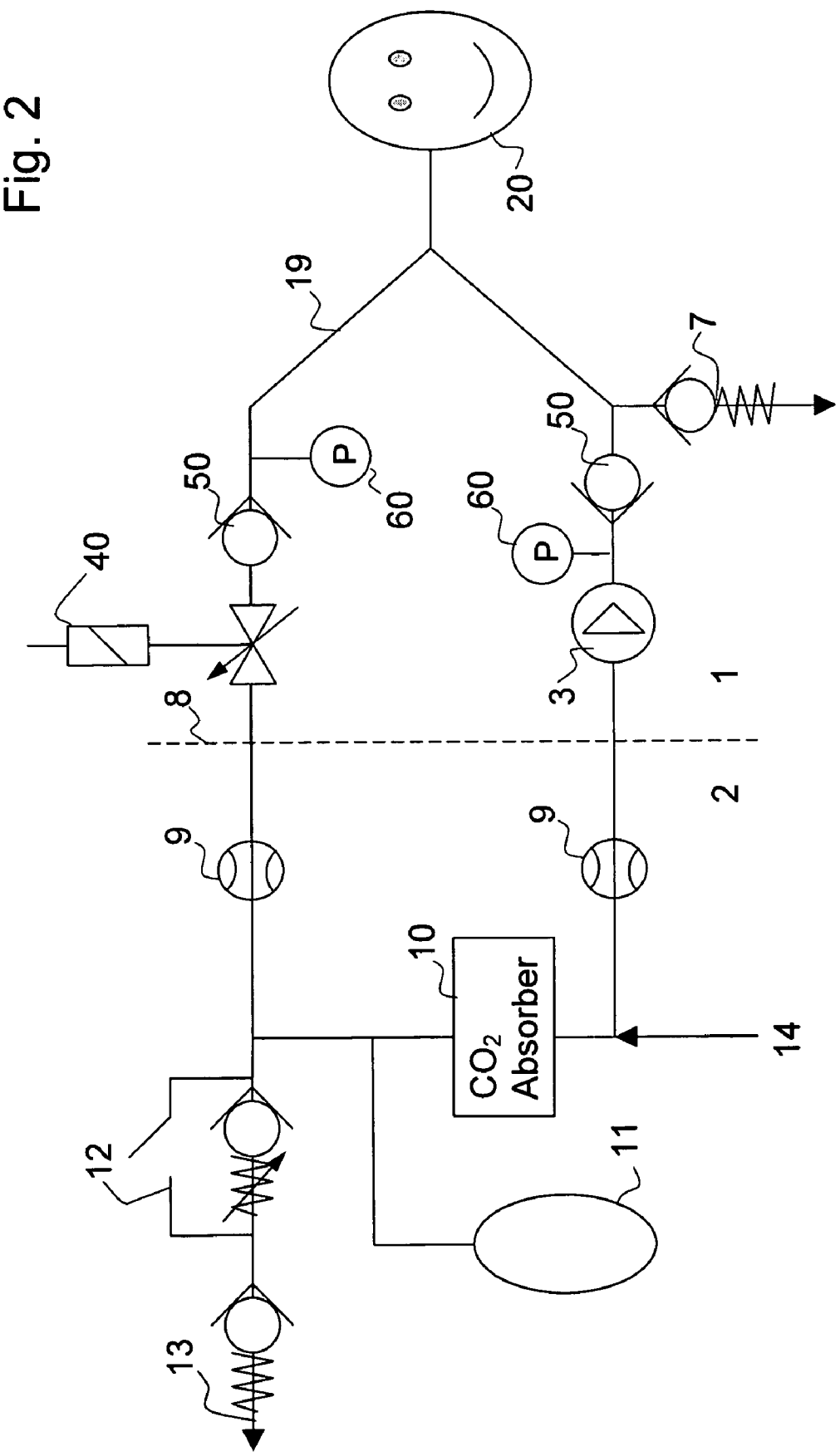
FIG. 2 is a schematic view showing a modular respiration system according to the invention designed as a rebreathing system.

FIG. 2 schematically shows the novel rebreathing system especially for use in anesthesia or in the surgical area in the assembled state with its two principal components, which are located in the mobile respiration module 1 and in the stationary part 2. The respiration drive 3, which is designed especially as a rotary compressor, which can be actuated dynamically, is located in the inspiration branch in the mobile respiration module 1. Following the direction of flow of gas, there is a first pressure sensor 60, a first non-return valve 50 and a pressure relief valve 7 on the way to the patient 20. The expired gas reaches the patient 20 via breathing tubes 19 and the PEEP (positive end-expiratory pressure) valve 40 from the patient via a second pressure sensor 60 as well as a second non-return valve 50. This valve 40 controls the breathing gas pressure and the breathing gas volume. The expired gas then reaches the stationary unit 2 via the connection interface 8. In the stationary part 2, it flows through a first flow sensor 9 into the manual breathing bag 11. Excess expired gas is sent into the excess gas discharge line 13 via the APL (airway pressure limit) valve 12 limiting the breathing gas pressure. The breathing gas for the next inspiration is sent again into the respiration drive 3 from the manual breathing bag 11 via a $CO_2$ absorber 10 and another, second flow sensor 9 and the connection interface 8. The fresh gas feed 14 is used to supply fresh gas, i.e., oxygen, air, laughing gas and/or anesthetic, into the respiration system.

Figure 3:
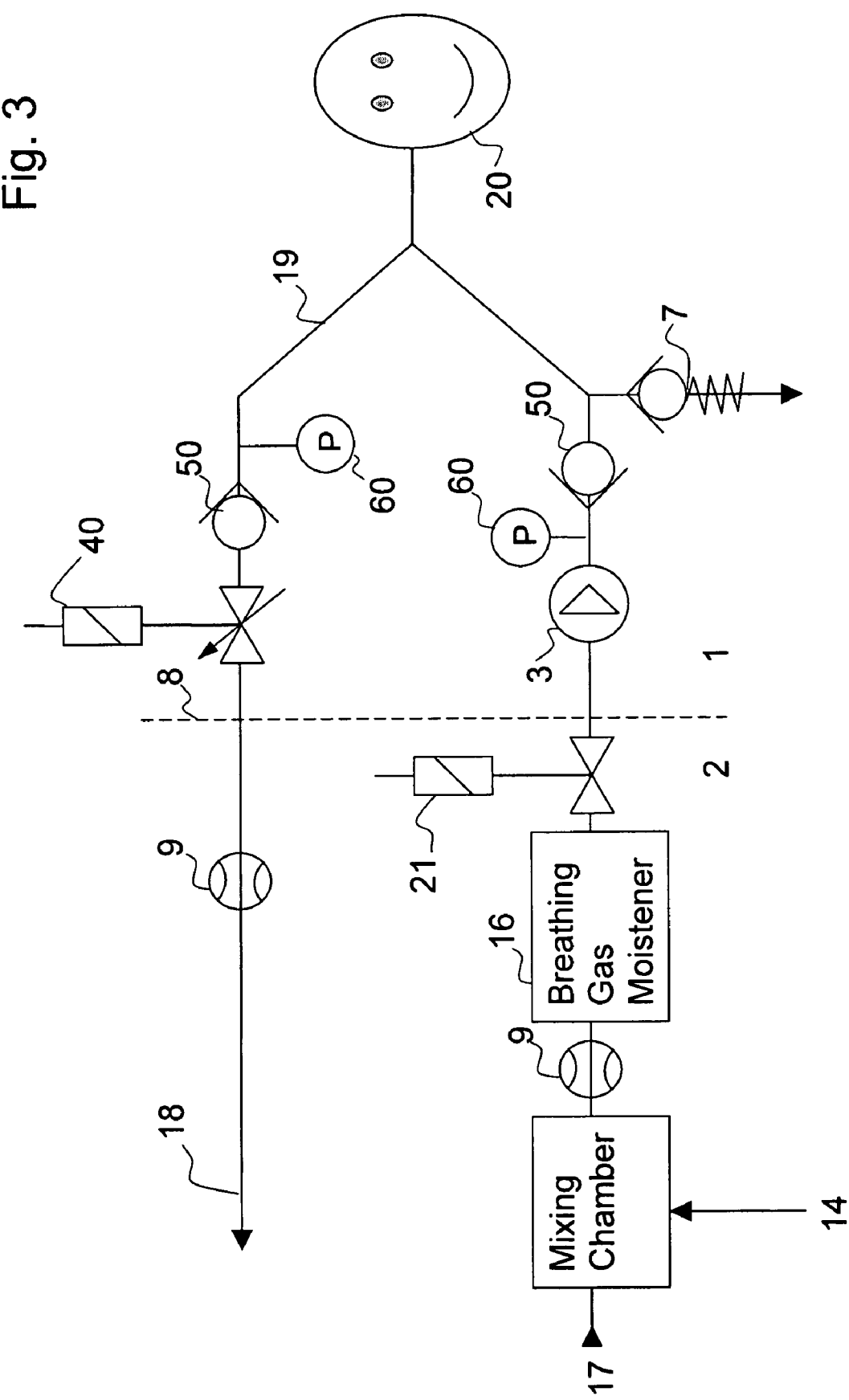
FIG. 3 is a schematic view showing a modular respiration system designed as an open respiration system.

FIG. 3 shows a respiration system without rebreathing, i.e., an open respiration system, for example, for use in the area of intensive care. The gas flow in the mobile respiration module 1 is identical to that in FIG. 2, but the stationary part 2 has a different design here. The inspiration gas is a mixture of ambient air 17 and fresh gas 14, here usually oxygen. The ambient air 17 is drawn in, for example, via a filter, not shown, by the respiration drive 3. Mixing with the fresh gas 14 takes place in a mixing chamber 15. The inspiration gas then enters the mobile respiration module 1 though the inlet-side inspiratory flow sensor 9, the breathing gas moistener 16, the occlusion valve 21 and the interface 8. The breathing gas moistener 16 is an option for long-term respiration, and the occlusion valve 21 is an option for measuring the lung function by briefly closing the inspiration line during the phase of inspiration (so-called p0.1 measurement). The expiration gas enters the environment or an expiration gas discharge line 18 during expiration from the mobile respiration module 1 through the interface 8 and the outlet-side, expiratory flow sensor 9 in the stationary part 2.

The flow sensors 9 according to the embodiments shown in FIGS. 2 and 3 are used to measure the breathing gas flow. The breathing pattern and the inspiratory volume flow or the inspiration volume are measured in the inspiration branch. The breathing pattern and the expiratory volume flow are measured in the expiration branch.

The leakage volume is determined from difference measurements. In addition, the flow sensors 9 provide data on the functional status and the reliability of operation of the respiration system.

While specific embodiments of the invention have been shown and described in detail to illustrate the application of the principles of the invention, it will be understood that the invention may be embodied otherwise without departing from such principles.

What is claimed is:

1. A modular respiration system for the mechanical respiration of a patient, the modular respiration system comprising:
    a mobile respiration module for connection to the patient, said mobile respiration module including a respiration system with a respiration drive, an inspiration branch, an expiration branch, an electrical energy supply unit and a memory with a control unit; and
    a first stationary part with an inspiration line, an expiration line, and means for detachably accommodating said mobile respiration module including a detachable connection interface for exchange of data, electric energy and breathing gases between said mobile respiration module and said first stationary part with said means for detachably accommodating said mobile respiration module, said detachable connection interface connecting said inspiration line to said inspiration branch, and connecting said expiration line to said expiration branch when said mobile respiration module is accommodated with said first stationary part, said expiration line and said inspiration line interconnected via a carbon dioxide absorber to form a rebreathing system in said first stationary part;
    a second stationary part with an inspiration line, an expiration line, and means for detachably accommodating said mobile respiration module including a detachable connection interface for exchange of data, electric energy and breathing gases between said mobile respiration module and said second stationary part with said means for detachably accommodating said mobile respiration module, said detachable connection interface connecting a respective said inspiration line to said inspiration branch, and connecting a respective said expiration line to said expiration branch when said mobile respiration module is accommodated with said second stationary part, said respective expiration line exiting to the environment from said second stationary part to form an open breathing system in said second stationary part.

2. A modular respiration system in accordance with claim 1, wherein said respiration system of said mobile respiration module comprises:
    a pressure relief valve in said inspiration branch with said respiration drive, and with breathing tubes to and from the patient when viewed in a direction of flow;
    a positive end expiratory pressure (PEEP) valve in said expiration branch; and
    a non-return valve arranged in or connected to said inspiration branch, said connection interface having a connection interface portion for said inspiration branch and said expiration branch.

3. A modular respiration system in accordance with claim 1, wherein said connection interface includes ports that are closed when said mobile respiration module has been mechanically accommodated in one of said stationary parts.

4. A modular respiration system in accordance with claim 1, wherein said mobile respiration module includes an operating device and at least one of a sensor part and a display part.

5. A modular respiration system in accordance with claim 1, wherein said respiration system of said mobile respiration module has a first pressure sensor and a first non-return valve operatively connected to said inspiration branch and a second pressure sensor and a second non-return valve operatively connected to said expiration branch.

6. A modular respiration system in accordance with claim 1, wherein said first stationary part comprises
    a first flow sensor with a manual breathing bag and an airway pressure limit (APL) valve inserted between said first flow sensor and said manual breathing bag, and with an excess gas discharge line as well as said carbon dioxide absorber being connected to said manual breathing bag and with a second flow sensor in the expiration line in a direction of flow.

7. A modular respiration system in accordance with claim 1, wherein said second stationary part is an open respiration system and comprises:
    a mixing chamber for ambient air and fresh gas;
    an inspiratory flow sensor;
    a breathing gas moistener and/or an occlusive valve in the inspiration line in a direction of flow; and
    an outlet-side expiratory flow sensor with outlet to said ambient air or into an expiration gas discharge line in the expiration line.

8. A modular respiration system in accordance with claim 1, wherein said respiration drive comprises a radial flow compressor that is actuated electrically.

9. A modular respiration system for the mechanical respiration of a patient, the modular respiration system comprising:
    a first stationary part including an inspiration line, an expiration line, and module accommodation means for accommodating a module, said module accommodation means including a detachable connection interface with a data exchange interface, an electric energy exchange interface and a breathing gas exchange interface for said inspiration line and said expiration line, said expiration line and said inspiration line interconnected via a carbon dioxide absorber to form a rebreathing system in said first stationary part;
    a second stationary part including an inspiration line, an expiration line, and module accommodation means for accommodating a module, said module accommodation means including a detachable connection interface with a data exchange interface, an electric energy exchange interface and a breathing gas exchange interface for said inspiration line and said expiration line, said expiration line exiting to the environment from said second stationary part to form an open breathing system in said second stationary part;

a mobile respiration module including a respiration drive, an electrical energy supply unit and a memory with a control unit, said respiration drive being connected to an inspiration branch and an expiration branch for connection to the patient, said mobile respiration module being selectively connectable to said first or second stationary part via a respective said module accommodation means via respective said data exchange interfaces, said electric energy exchange interfaces and said breathing gas exchange interfaces, a respective said breathing gas exchange connecting said inspiration line to a respective said inspiration branch, and connecting said expiration line to a respective said expiration branch when said mobile respiration module is connected to said respective stationary part.

10. A modular respiration system in accordance with claim 9, wherein said inspiration branch connected to said respiration drive includes a pressure relief valve with breathing tubes to and from the patient when viewed in a direction of flow and said expiration branch has a positive end expiratory pressure (PEEP) valve and wherein a non-return valve is arranged in or connected to said inspiration branch, said connection interface having a connection interface portion for said inspiration branch and said expiration branch for connecting said inspiration branch and said expiration branch to one of said stationary parts.

11. A modular respiration system in accordance with claim 9, wherein said connection interface includes ports that are closed when said mobile respiration module has been mechanically accommodated in one of said stationary parts.

12. A modular respiration system in accordance with claim 9, wherein said mobile respiration module includes an operating device and at least one of a sensor part and a display part.

13. A modular respiration system in accordance with claim 9, wherein said mobile respiration module has a first pressure sensor and a first non-return valve operatively connected to said inspiration branch and a second pressure sensor and a second non-return valve operatively connected to said expiration branch.

14. A modular respiration system in accordance with claim 9, wherein said first stationary part has a first flow sensor with a manual breathing bag and an airway pressure limit (APL) valve inserted between said first flow sensor and said manual breathing bag, and with an excess gas discharge line as well as a said carbon dioxide absorber being connected to said manual breathing bag, and with a second flow sensor in the expiration line in a direction of flow.

15. A modular respiration system in accordance with claim 9, wherein said second stationary part is an open respiration system and comprises:
- a mixing chamber for ambient air and fresh gas;
- an inspiratory flow sensor;
- a breathing gas moistener and/or an occlusive valve in the inspiration line in a direction of flow; and
- an outlet-side expiratory flow sensor with outlet to said ambient air or into an expiration gas discharge line in the expiration line.

16. A modular respiration system in accordance with claim 9, wherein said respiration drive comprises a radial flow compressor that is actuated electrically.

* * * * *